United States Patent [19]

Shuler et al.

[11] Patent Number: 5,747,281
[45] Date of Patent: May 5, 1998

[54] SYSTEM USEFUL FOR THE PRODUCTION OF PROTEINS FROM RECOMBINANT DNA IN SINGLE CELLED ORGANISMS

[75] Inventors: Michael L. Shuler; David B. Wilson, both of Ithaca, N.Y.

[73] Assignee: Cornell Research Foundation, Inc., Ithaca, N.Y.

[21] Appl. No.: 472,485

[22] Filed: Jun. 7, 1995

Related U.S. Application Data

[63] Continuation of Ser. No. 471,900, Mar. 12, 1990, which is a continuation of Ser. No. 353,203, May 12, 1989, abandoned, which is a continuation of Ser. No. 655,281, Sep. 28, 1984, abandoned.

[51] Int. Cl.$^6$ .................. C12P 21/00; C12N 15/00
[52] U.S. Cl. .................. 435/69.1; 435/172.3; 435/252.3
[58] Field of Search .................. 435/69.1–69.52, 435/172.1, 172.3, 252.3–252.35, 243, 174, 176, 177, 320.1; 935/40, 43, 47, 48, 66, 72, 73

[56] References Cited

U.S. PATENT DOCUMENTS 4,595,658  6/1986  Zinder et al. .................. 435/69.1

OTHER PUBLICATIONS

Kudo et al., J. Bacteriol. 156: 949 (1983).
Kato et al., Eur. J. Microbiol. Biotechnol. 18: 399 (1983).

*Primary Examiner*—James Martinell
*Attorney, Agent, or Firm*—Nixon, Hargrave, Devans & Doyle

[57] ABSTRACT

A single celled organism, vector, and method are provided for continuous production of excreted proteins in the absence of substantial host cell replication and without the necessity for the addition of antibiotics to control cell replication. The vector has (1) an inducible promoter capable of activating a gene for a protein to be produced under conditions that substantially inhibit host cell replication, and (2) a hybrid gene containing a signal sequence fused to a gene for the protein to be produced. Large quantities of the transformed single celled organisms containing the vector can be grown in the absence of inducing conditions, thereby reducing the problem of plasmid loss. Further, the protein is produced under conditions that substantially inhibit host cell replication, thereby allowing immobilization of the single celled organism by entrapment or attachment within or onto a solid support surface. The single celled organism can be immobilized after, before or simultaneously with induction. The single celled organism advantageously may be an encapsulated gram-negative bacterium which has no outer membrane or an outer membrane that is permeable to the proteins to be produced so that the protein products are excreted into the media thereby avoiding difficulty in recovering the desired protein products due to the formation of inclusion bodies or the presence of contaminants produced by cell lyses.

24 Claims, 5 Drawing Sheets

SYSTEM USEFUL FOR THE PRODUCTION OF PROTEINS FROM RECOMBINANT DNA IN SINGLE CELLED ORGANISMS

This is a continuation of application Ser. No. 07/471,900 filed on Mar. 12, 1990, which was a continuation of application Ser. No. 07/353,203, filed May 12, 1989, now abandoned, which was a continuation of application Ser. No. 06/655,281, filed Sep. 28, 1984, now abandoned.

FIELD OF THE INVENTION

The present invention relates generally to a single celled organism, vector, and method for the production of excreted proteins from single celled organisms, and, in particular, the present invention relates to a single celled organism containing a vector such that proteins are continuously expressed by the vector in the absence of substantial host cell replication. Advantageously, the single celled organism can be a gram-negative bacterium having no outer membrane or an outer membrane that is permeable to the protein to be produced.

BACKGROUND OF THE INVENTION

The large-scale production of proteins as the result of the use of recombinant DNA technology in bacteria faces several difficulties including: (1) overgrowth of the culture by revertant bateria and bacteria that have lost the recombinant DNA plasmid due to genetic instability of the transformed strain; (2) difficulty in recovering the desired protein products in an active form due to the formation of inclusion bodies; and (3) difficulties in recovering the protein product without contaminants due to the necessity of having to lyse the bacteria in order to isolate the product.

Actively growing bacteria containing recombinant DNA plasmids grow more slowly than those without the recombinant DNA plasmids when the proteins coded by the recombinant DNA are being actively manufactured. Therefore, large quantities of bacteria can be difficult to produce without potential problems of plasmid instability. If a plasmid gene is expressed continuously, a high proportion of the plasmid protein is produced by the bacterium as the product. However, because the bacterium has diverted substantial resources away from its own growth, the bacterium grows more slowly than it otherwise would.

Further, some bacteria may spontaneously lose the plasmid and revert to the parental form which grows more rapidly. For example, a bacterium containing free plasmids can lose the plasmids at a rate of 1 out of $10^7$ or $10^6$ divisions or even more frequently than one out of $10^6$ divisions. (See, for example, L. C. Klotz, *Ann. N.Y. Acad. Sci.*, 369 p.1 (1983)). Therefore, the more rapidly growing, but non-productive, revertant bacteria soon displace the plasmid-bearing bacteria. The problem of plasmid or vector loss becomes increasingly important as the scale of operation increases, making continuous culture processes practically impossible for large-scale batch cultures.

Additionally, *Escherichia coli* (hereinafter *E. coli*) is presently the organism of choice for genetic manipulation. A wide range of vectors, promoters, etc., and a detailed knowledge of the genetic system and physiology allow for elegant genetic manipulation of *E. coli*. However, *E. coli* and other gram-negative bacteria do not normally excrete the proteins produced from the cells, and, therefore, the bacterial cells must be ruptured to obtain the product of interest. Consequently, the product must be recovered from an aqueous solution containing many macromolecules in addition to the desired product. In particular, recovery of a product sufficiently free of contaminants (such as, for example, endotoxins) to be useful in therapeutic or food applications is difficult. Also, resolubilizing the isolated proteins in an active form is often extremely difficult because proteins formed from recombinant DNA molecules which remain within the cell form inclusion bodies.

One method which is known for synthesizing within a bacterial host, and excreting through the membrane of the host, a selected protein or polypeptide is disclosed in U.S. Pat. No. 4,338,397 and European Patent Application 0,038, 182 A2 (1981). The method involves forming a cloning vehicle wherein a non-bacterial DNA fragment which codes for the precursor of the selected protein or polypeptide, including the signal sequence of the selected protein or polypeptide, is inserted behind a promoter of either a bacterial or phage gene within a cloning vehicle or a DNA fragment of the bacterial or phage gene. The method produces mature proteins or polypeptides free of signal sequences or other chemical substituents. However, the majority of the selected protein or polypeptide, i.e. as much as 90%, is found in the periplasmic space of the host cells, rather than being secreted beyond the host cell membrane into the culture medium. Further, these patent documents disclose that the bacterial host cells must be actively growing, and, therefore, cannot be immobilized without the attendant difficulties of the bacterial cells dividing and thereby possibly clogging the protein production system.

U.S. Pat. No. 4,336,336 discloses a fused gene for producing excreted proteins in bacteria. The fused gene is created by fusing a gene for a cytoplasmic protein to a gene for a non-cytoplasmic protein. However, when gram-negative bacteria are used, the genes for the non-cytoplasmic protein are those coding for proteins that travel to the cell surface or periplasmic space and, therefore, the proteins thus produced are not actually excreted from the cell. Further, the bacteria must be actively growing in order to produce the protein, and, the protein thus produced contains an $NH_2$-terminus coded for by the carrier protein.

PCT Application WO 80/00030 also describes a method for producing excreted proteins from a fused gene. According to the disclosure, a plasmid is constructed which contains a DNA sequence coding for a selected protein from a eukaryotic cell inserted into a cleaved gene representing a periplasmic or extracellular bacterial protein. Only secretion of the protein into the periplasmic space is actually demonstrated for *E. coli* and not excretion into the medium. Further, continous protein production is neither taught nor suggested.

European Patent Application 0 036 259 A2 (1981) discloses a method and vector for producing a gene product which, if produced in gram-positive bacteria, can be recovered from the growth medium. The gene for the protein to be produced is under the control of an operator, promoter, and ribosomal binding site sequence. Further, the protein to be produced is under the control of a transport mechanism by which the protein is secreted by the host strain. The method is applicable to gram-negative bacteria. However, when gram-negative bacteria are used, the protein is secreted into the periplasmic space instead of the growth medium.

United Kingdom Patent Application 2 091 269 A discloses various plasmid cloning vehicles for the expression of exogenous genes in transforming bacterial hosts. The cloning vehicles comprise a DNA insert fragment coding for the desired polypeptide linked in reading phase with one or more functional fragments derived from an outer membrane protein gene of a gram-negative bacterium. The polypeptide thus produced is expressed with a leader sequence located at the amino terminal such that the desired product is secreted through the cytoplasmic membrane into the periplasmic space or into the cell's outer membrane. Further, it is suggested that the use of a host cell known to be "leaky" may be desirable in that proteins secreted across the cytoplasmic membrane of such cells may ultimately "leak" out into the culture medium through the outer membrane of the cell. However, this patent document does not in any way teach or suggest the possibility of continuous protein production.

It is also known that the addition of various antibiotics to the growth medium of *Bacillus subtilis* cells carrying plasmids coding for rat proinsulin can inhibit bacterial cell division while allowing continued protein synthesis and excretion of the proteins, even when the microorganisms are immobilized in various support materials including alginate, polyacrylamide and agarose supports. Additionally, an immobilized genetically engineered strain of a periplasmic leaky mutant of *E. coli* is known to maintain protein synthesis and excrete the protein into the medium even though cell growth has been arrested by addition of nalidixic acid to the growth medium. Mosbach, K., et al, "Formation of Proinsulin by Immobilized *Bacillus subtilis*", Nature, 302, 543 (April 1983). However, this system does not solve the problem of plasmid or vector loss while culturing the bacteria to obtain large quantities of transformed cells. Additionally, the method described in Mosbach et al, supra, is disadvantageous in that antibiotics have undesirable side reactions at higher concentrations. Most antibiotics targeted to stop DNA replication will, at sufficient concentration, also affect DNA transcription and consequently protein production. Further, antibiotics are expensive and the high costs would limit the technique of Mosbach et al, supra, to high-value, small-volume protein products.

In addition to the above described methods, several other patent documents are directed to immobilizing cells in a resting or growing state or in a non-viable form as carriers for enzymes. (See for example U.S. Pat. No. 4,347,320, German OLS 28 35 874 A1 (1980) and 28 35 875 A1 (1980)). However, none of these patent documents teaches or discloses the immobilization of L-forms, spheroplasts, leaky mutants, or other forms in which the cell envelope has been altered to allow protein excretion. Further, none of these patents disclose cells which produce proteins.

SUMMARY OF THE INVENTION

Accordingly, one object of the present invention is to provide a system for the continuous production of proteins from recombinant DNA wherein large quantities of transformed cells can be obtained without the difficulty of plasmid loss.

Another object of the present invention is to provide a system for the continuous production of proteins from recombinant DNA wherein production of the desired protein product occurs while host cell replication is inhibited.

Still another object of the present invention is to provide a system for the continuous production of proteins from recombinant DNA in gram-negative bacteria wherein the proteins are excreted into the culture medium.

An even further object of the present invention is to provide an immobilized cell system for producing excreted proteins which can be operated on a continuous basis, does not have the disadvantages of the necessity for use of antibiotics, and offers economic advantages over batch cultivation methods.

These and other objects of the present invention are achieved by providing, in one embodiment, a single celled organism for continuous production of excreted proteins in the absence of substantial host cell replication and without the necessity for the addition of antibiotics to control cell replication. The cell replication can be controlled, for example, by nutrient limitation or temperature shifts. The single celled organism has no outer membrane, an incomplete outer membrane, or an outer membrane which is permeable to the proteins to be produced and contains a vector comprising: (a) an inducible promoter capable of activating a gene for a protein to be produced under nutrient and/or temperature conditions that substantially inhibit host cell replication; and (b) a hybrid gene containing a signal sequence fused to the gene for the protein to be produced.

According to the present invention, there is also provided a method for continuous production of excreted proteins in the absence of substantial host cell replication and without the necessity for the addition of antibiotics to control cell replication comprising: (1) culturing, under non-inducing conditions for the protein to be produced, a single celled organism containing a vector comprising (a) an inducible promoter capable of activating a gene for a protein to be produced under nutrient and/or temperature conditions that substantially inhibit host cell replication and (b) a hybrid gene containing a signal sequence fused to the gene for the protein to be produced, wherein (i) prior to culturing, the single celled organism has no outer membrane, or has an outer membrane which is permeable to the proteins to be produced or (ii) prior to culturing, the single celled organism has an outer membrane and toward the end of or after culturing, the single celled organism is treated to remove all or part of the outer membrane or to render the outer membrane permeable to the proteins to be produced; (2) inducing the single celled organism containing the plasmid; and (3) producing the proteins in the absence of substantial host cell replication.

In a preferred embodiment, the method further comprises the step of immobilizing the single celled organism-vector system described above and inducing synthesis of the desired protein. Generally, induction occurs before immobilization, but induction can also occur after or simultaneously with immobilization.

BRIEF DESCRIPTION OF THE FIGURES

In the Figures all reference numbers represent the same general elements.

FIG. 1 is a schemmatic representation of one preferred embodiment of the process of the present invention. A plasmid, 1, is constructed having an inducible promoter, 2, and a hybrid gene containing a signal sequence, 3, fused to a gene, 4, for the protein to be produced. The hybrid gene containing a signal sequence fused to the gene for the protein to be produced is inserted into a bacterium, 5, having an outer envelope, 6, to form a transformed bacterium, 7. The transformed bacterium is cultured under non-inducing conditions for the protein to be produced to provide a large quantity of bacteria. Next, part of the outer membrane, 6, is removed from the bacterium containing the plasmid to provide L-forms, 8. A large quantity of bacteria is grown. The L-forms are induced and then immobilized to form immobilized bacteria, 9, which are then maintained in a reactor, 10, in a metabolically active, but non-replicating, state in order to produce protein products which are recovered without having to lyse or otherwise destroy the entrapped bacteria.

FIG. 3 is a third embodiment of the present invention. In this embodiment, a bacterium with a faulty or leaky outer membrane is formed by inducing protein production just prior to entering the stationary phase while culturing a large quantity of transformed cells.

DETAILED DESCRIPTION OF THE INVENTION

In this detailed description, the following definitions apply:

Outer Membrane—The term "outer membrane", as used herein, means the membrane (composed primarily of lipopolysaccharides, phospholipids, lipoprotein, and specific membrane proteins) which is farthest from the center of a gram-negative cell. This type of membrane is found in gram-negative bacteria where the cell envelope consists of an inner or cytoplasmic membrane, a single layer of peptidoglycan, and an outer membrane. The structure of the cell envelope in gram negative cells has been reviewed by DiRienzo, J. M., et al. (Ann. Rev. Biochem. 47:481–532, 1978). One of the primary functions of the outer membrane is the retention of macromolecules such as protein within the cell.

L-Form—The term "L-form", as used herein, means a bacterium, either gram-positive or gram-negative, that has lost the capability to manufacture a functional cell wall or envelope. L-forms have irregular shapes. Generally the peptidoglycan layer is not made or is made with an irregular shape. Such forms may be stable or revertible; stable-forms are preferred for this invention. Methods to obtain L-forms in high yield are known (J. C. Makemson and R. Z. Darwish, Infect. Immun. 6:880 (1972)).

Spheroplast—The term "Spheroplast", as used herein, means the cell that results from the treatment of some gram-negative bacteria with lysozyme which chemically attacks the peptidoglycan layer. Such cells assume a spherical shape if a high salt solution surrounds the cell, preventing osmotic breakage. Spheroplasts are capable of limited multiplication. Gram-positive cells subjected to lysozyme treatment lose the whole cell wall and are called "protoplasts". Spheroplasts differ from L-forms in that the spheroplast has the capability of forming a normal cell envelope and is spherical in shape, while L-forms are generally irregular in shape.

Periplasmic-Leaky Mutant—The term "Periplasmic-Leaky Mutant" (or simply "Leaky Mutant"), as used herein, means a cell with an altered cell envelope that allows certain proteins to escape the cell and enter the external culture medium. The cell is substantially similar in shape to unmutated cells. Most often the proteins released are "periplasmic proteins" that normally would be trapped between the cytoplasmic membrane and the peptidoglycan/outer membrane layer.

Temperature-Sensitive Mutant—The term "Temperature-Sensitive Mutant", as used herein, means a cell that cannot replicate itself normally at a given temperature while still maintaining active protein synthesis. DNA temperature-sensitive mutants would be prime examples of these types of mutants.

Inducible Promoter—The term "Inducible Promoter", as used herein, means a promoter site which is activated directly by the presence or absence of a chemical agent or indirectly by an environmental stimulus such as temperature changes. A promoter is the region of DNA at which the enzyme RNA polymerase binds and initiates the process of gene transcription. As used in this application, the term promoter also includes an appropriate ribosome binding site and $d_1$ and $d_2$ distances. The region of DNA separating the site at which RNA polymerase binds and the ribosome binding site is known as $d_1$. The region of DNA separating the ribosome binding site and the actual gene is known as $d_2$. The sum of these four regions represents the control region and for simplicity will be called the promoter in this document.

Nutrient Starvation Inducible Promoter—The term "Nutrient Starvation Inducible Promoter", as used herein, means an inducible promoter which is activated when the cellular concentration of a chemical agent necessary for cellular functioning is reduced to a low level. A low level as used herein means the concentration of the nutrient such that the rate of cell replication is significantly reduced from the rate measured when an abundance of the nutrient is available, e.g., at a growth rate limiting level. Environmental stimuli variables such as temperature are also included.

Phosphate Starvation Inducible Promoter—The term "Phosphate Starvation Inducible Promoter", as used herein, means an inducible promoter activated when the intracellular concentration of phosphate drops to a low level.

Signal Sequence—The term "Signal Sequence", as used herein, means a sequence of amino acids which when attached to a given protein allows the passage of that protein from within the cell cytoplasm through the inner or cytoplasmic membrane into the periplasmic space. A signal sequence is sometimes called a leader or a leader sequence.

Vector—The term "Vector", as used herein, means an extrachromosonal piece of DNA, examples of which are plasmids, bacteriophage λ, cosmids, and single-stranded bacteriophages.

Although the invention is described by reference to bacteria, one of ordinary skill in the art will appreciate that the invention applies to any single celled organism including any organisms that can be cultured as single cells (or small aggregates of cells).

In accordance with this invention, any single celled organism may be used. However, a particularly useful embodiment of the invention employs a gram-negative bacterium. According to a preferred embodiment of the invention, the gram-negative bacterium is E. coli. According to a more preferred embodiment of the invention, the E. coli bacterium is E. coli K-12 or K-12 derivatives. When using the tac promoter or other IPTG inducible promoter on the plasmid, E. coli RB791, which overproduces the lac repressor is preferred. Examples of gram-positive and gram-negative bacterial species as well as lower eukaryotes that could be used include: Bacillus subtilis, Saccharomyces cerevisiae, Streptomyces (e.g., S. griseus), Fusarium oxysporum, Pseudomonas (e.g., P. putida or P. olevorans) and Clostriduim perfringens. However, many other single celled organism not specifically mentioned could be used in the invention.

Further, in accordance with this invention, when the bacterium has an outer membrane that is not permeable to the protein to be produced, the outer membrane is removed or made permeable to the proteins to be excreted. Suitable forms of such bacteria include L-forms, spheroplasts, leaky mutants and cells whose outer membrane is disrupted by the induction of a high level of plasmid encoded protein synthesis where the protein contains a functional signal sequence. Methods for producing L-forms, spheroplasts, leaky mutants, and cells whose outer membrane is disrupted by the the induction of a high level of plasmid encoded protein synthesis where the protein contains a functional signal sequence are described below.

Also in accordance with this invention any vector can be used that contains: (a) an inducible promoter which activates a gene for the protein to be produced in response to inducing conditions that also result in the inhibition of host ell replication; (b) a hybrid gene containing a signal sequence fused to the gene for the protein to be produced. Examples of suitable vectors are derivatives of pBR322. For example, the plasmid pKK is produced by inserting a hybrid trp-lac (tac) promoter (E. Ammon., J. Brosius, and M. Ptashne, *Gene* 25:167–178 (1983) between the Eco RI and Hin III sites of pBR322.

Another useful vector is the plasmid pMMB22 (M. M. Bagdasarian, et al, *Gene* 26:273–282 (1983)). Other possible vectors are: pAT153 (A. J. Twigg and D. Sherratt, *Nature* 283:216 (1980)); pPLa 2311 (E. Remaut, et al., *Gene* 15:81 (1981)); ptac12 (T. Maniatis, et al., *Molecular Cloning* (1982)); ptrpL1 (J. C. Edman, et al., *Nature* 291:503 (1981)); pNCV (D. V. Goeddel, et al., *Nature* 287:411 (1980)); bacteriophage λ varients (e.g., λgt wes.λB (P. Leder, D. Tiemeier, and L. Enquist, *Science* 196:175 (1977)) or λL471 (W. A. Loenen and W. J. Braminar, *Gene* 10:249 (1980)); the cosmid MUA-3 (Meyerawitz, et al.), *Gene* 11:271 (1980)); and the single-stranded bacteriophage M13 (S. Anderson, et al., *Nucleic Acids Res.* 8:1731 (1980)). Generally, plasmids are preferred vectors for expression and most likely to be used in the invention. Cosmids and bacteriophage λ are normally used to construct and propagate libraries of eukaryotic genomic DNA although they could be used for protein expression. Single-stranded bacteriophages are utilized primarily for sequencing and as sources of strand-specific probes for nucleic acid hybridization.

The vector can contain any inducible promoter with appropriate ribosomal binding sites such as the Shine-Delgarno sequence (J. Shine an L. Dalgarno, *Nature* 154:34 (1975)) and with appropriate spaces between the promoter and ribosomal binding sites and between the ribosomal binding sites and the gene for the signal sequence and which is capable of activating the genes of interest in the absence of substantial host cell replication. The inducible promoter can be such that the conditions inducing the promoter also inhibit substantial host cell replication or the inducible promoter can be such that an inducer can be added simultaneously with alterations in conditions such as nutrients or temperature that inhibit substantial host cell replication. In this manner, the gene for the protein product of interest would not be expressed during cell growth, but upon purposefully subjecting the host cell to inducing conditions, cell replication is substantially inhibited and formation of the desired protein product induced.

The ribosome binding site and the correct spacing in the control element are described by L. C. Klotz (*Annuals N.Y. Acad. Sci.* 413:1 (1983)) and T. Maniatis, et al., *Molecular Cloning* (1982)). The optimal $d_2$ distance is given by H. M. Shapard, et al., (DNA 1:125 (1982)). Further, details of appropriate sequences and spacing for effective mRNA synthesis are given by J. A. Steitz in *Biological Regulation and Development* (ed. R. F. Goldberger), Vol. 1, p. 349, Plenum Press, N.Y. (1979); T. M. Roberts, et al., *Proc. Natl. Acad. Sci.*, 76, pp. 760 and 5596 (1979); L. Guarente, et al., *Science* 209:1428 (1980) and *Cell* 20:543 (1980); and L. Gold, et al., *Annu. Rev. Microbiol.* 35:365 (1981). strong well controlled promoters that can be used are described by T. Maniatis, et al., *Molecular Cloning* (1982) and in a volume edited by R. L. Rodriguez and M. I. Chamberlin, *Promoter Structure and Function*, Proeger Publishers, N.Y., N.Y. (1982).

Replication need not be completely inhibited. Rather, replication need only be substantially inhibited. By substantial inhibition it is meant that the rate of cell duplication must be sufficiently low to prevent disruption of the matrix the cells are entrapped within or attached to and to prevent the escape of cells into the liquid medium in sufficient numbers to interfere with protein recovery. A simple means of assessment would be to operate a laboratory column for a substantial period of time (e.g., greater than two weeks) and then determine whether the number of cells has changed and whether this change has physically damaged the matrix (e.g., fewer particles, cells growing outside of the matrix, membranes showing holes or tears, beads broken into parts, etc.).

Examples of such inducible promoters include lac (see, e.g., K. Backman and M. Ptashne, *Cell* 13:65 (1978)); λP$_L$ (see, e.g., E. Remaut, P. Stanssesns, and W. Fiers, *Gene* 15:81 (1981); trp (see, e.g., D. G. Kleid, et al, *Science* 214:1125 (1981)); and tac (see, e.g., H. A. deBoer, et al, In *Promoters, Structure, and Function*, R. L. Rodriguez and M. J. Chamberlin, Eds., Praeger Publishers, N.Y., N.Y. (1982)). Preferably, the vector contains a nutrient starvation inducible promoter which does not also prevent protein synthesis such as a phosphate starvation inducible promoter. An example of a phosphate starvation inducible promoter useful in the present invention is pho A. The vector carrying the pho A promoter should also contain the pho B and pho R regulatory genes. This is because without the protein products from the regulatory genes, the promoter cannot be efficiently switched on or off. Over-expression of the gene leads to cell death. A number of other promoters inducible by phosphate starvation are known (e.g., B. L. Wanner and R. McSharry, *Journal Molecular Biology* 158:347–363 (1982)).

Promoters induced by limiting iron, zinc, calcium, magnesium, etc., might exist and would be useful in the present invention.

The nutrient which is limited would be fed to the reactor at a concentration sufficient to maintain viability but not so high as to permit significant cell replication. The proper amount is readiliy determined by one skilled in the art.

A temperature inducible promoter also can be used. An example of a known temperature inducible promoter is λP$_L$ in a host which contains temperature-sensitive λ repressor (e.g., λcIts857, see, Bernard et al, *Gene*, 5:59 (1979)).

Chemically activated inducible promoters such as the lac or tac promoters which are activated by addition of isopropyl-β-D-thiogalactoside (IPTG) can also be used.

Another example of chemically activated inducible promoter is the trp promoter which can be induced with 3-indolylacetic acid or by starvation for tryptophan. Other chemically inducible promoters include those for galactose and arabinose. Other variants of the lac promoter, e.g., lacUV5, can also be induced by IPTG.

As the signal sequence, signal sequences which come from *E. coli* for any periplasmic or outer membrane protein should be useful and are likely to be preferred. It is also possible to use hybrid signal (or leader) sequences. Konrad (*Annuals New York Academy of Sciences* 413:12–22 (1983))

reports on a signal sequence with a fusion of the first 12 amino acids of the β-lactamase signal sequence (from *E. coli*) to the last 13 amino acids of an insulin signal sequence (from humans). The fused signal sequence is effective in allowing the protein to pass through the inner membrane.

For bacteria, the preferred signal sequence is that for β-lactamase. This protein is apparently excreted after it has been synthesized completely in the cytoplasm (post-translational export) (D. Koshland and D. Botstein, *Cell* 30:893–902 (1982)). A number of mutations of the β-lactamase signal sequence that increase the rate of export have been characterized (D. Koshland and D. Botstein, *Cell* 30:903–914 (1982)). These sequences are also suitable in this invention. Thus proteins attached to a β-lactamase signal could be exported without relying on other downstream signals coded by the vector. Leader sequences from non-bacterial sources are useful in the present invention if the sequences can function in the host.

In accordance with known techniques, the gene for the protein to be produced is inserted after the DNA coding for the signal sequence in a vector which contains the desired inducible promoter linked to the DNA coding for the signal sequence fused to the gene of interest. The gene of interest can be fused to the gene for the signal sequence of choice by known techniques, for example, see T. J. Silhavy, P. J. Barsford, Jr., and J. R. Beckwith in *"Bacterial Outer Membranes:*, M. Inoye, Ed., p. 203, Wiley, New York, 1979 and/or E. T. Palva and T. J. Silhary, *Molecular Gen. Genetics* 194:388 (1984). In some cases a short portion of the β-lactamase signal can be fused to the natural leader sequence of a foreign protein (Konrad, *Annals New York Academy of Science* 413:12–22(1983)). These can be used in the present invention.

The protein to be produced can be specific to the host or can be from other eukaryotic or procaryotic cells.

The vector can be constructed by commonly known methods. In general, the appropriate promoter and the structural gene of interest are ligated in a commonly used plasmid such as pBR322 carrying suitable restriction sites and/or linkers. A number of techniques are described by T. Maniatis, E. F. Fritch, and J. Sombrook, *Molecular Cloning*, Cold Spring Harbor Laboratory (1982). Specific examples of methods for producing plasmids useful in the present invention are described in the Ammon and Bogdasarian articles cited above.

The vector is inserted into the host bacterium by conventionally known methods, for example, the standard calcium transformation procedure for *E. coli* strains related to K-12 (T. Maniatis, E. F. Fritch, and J. Sombrok, *Molecular Cloning*, Cold Spring Harbor Laboratory (1982)).

For *E. coli* strains with an intact restriction system such as *E. coli* B and derivatives thereof a more involved approach is necessary. For example, the approach requires the use of a B derivative strain, *E. coli* WA837 which is restriction⁻ and methylase⁺. A plasmid inserted into and recovered from *E. coli* WA837 can be used in the transformation of other B derivatives since the modified plasmid will not be attacked by the host restriction system.

An alternate method is transduction with a phage (see T. Maniatis, et al., *Molecular Cloning* (1982)). Transduction is typically done with λ or P1 in *E. coli*.

Transformation is the most general method for introducing DNA to other microbes besides *E. coli*. Some bacteria are naturally competent and DNA uptake is easily accomplished (e.g., *Bacillus subtilis*, see C. Anagnostopoulos and J. Spizizen, *J. Bacteriol.* 81:74 (1961). Using methods to protect the foreign DNA from cellular nucleases transformation can be accomplished. With competent strains transformation does not require calcium treatment. Transformation schemes have been developed from many other genera; for example, Streptomyces, (K. F. Chafer, et al., *Curv. Top. Microbiol. Immunol.* 96:69 (1982)); Streptococcus (D. B. Clewell, *Microbiol. Rev.* 45:409 (1984)); Staphylococcus (M. Lindberg and R. P. Novick, *J. Bacteriol.* 115:139 (1973); and Clostridium (D. L. Heefner, *J. Bacteriol.* 159:460 (1984)). In some cases protoplast fusion can be used (see S. Chang and S. N. Cohen, *Molec. Gen. Genet.* 168:111 (1979)). An alternate, less frequently utilized scheme, is to transform the DNA into one organism, such as *E. coli*, and then transfer the DNA to a second organism through conjugation. A description of methods for gene transfer are given in P. Gerhardt, *Manual of Methods for General Bacteriology*, Am. Soc. for Microbiol., Washington, D.C. (1981).

The bacterium or other single celled organism containing the vector is then cultured in the absence of inducing conditions for the protein to be produced in order to obtain a quantity of bacteria or other single celled organism sufficient to produce the desired amount of protein. The amount of bacteria or other single celled organism is easily determined by one skilled in the art.

The culture medium is any commonly used culture medium such as M9 buffer plus fructose (20 g/100 l) and casein amino acids (20 g/100 l). Suitable media for culturing *E. coli* are given by T. Maniatis, et al., *Molecular Cloning*. The appropriate media for other strains is host dependent. Suitable medium for different species are given by P. Gerhardt, et al., *Manual of Methods for General Bacteriology*, Am. Soc. for Microbiol., Washington, D.C. (1981).

After the desired quantity of bacteria for protein production is obtained, the outer envelope of gram-negative bacteria can be removed by commonly known methods. Spheroplasts and protoplasts can be obtained from treatment of gram-negative and gram-positive cells, respectively. Spheroplasts can be obtained by a variety of methods involving among others penicillin or lysozyme-EDTA treatment. Descriptions of the relevant procedures can be found in R. Respeske, *Biochim. et. Biophys. Acta* 30, 225, 1958, J. Spizizen; *Meth. in Enz.* 5, 122 (1962), or for procedures particularly applicable to *E. coli*, in H. R. Kaback, *Meth. in Enz.* 22, 99–120 (1972). To keep cells from bursting, they must be maintained in an osmotically compatible medium (e.g., 1.17 M sucrose). Such cells are very fragile and capable of only limited multiplication.

An alternative to spheroplasts are L-forms. L-forms can be cultured initially or produced after a volume of bacteria is obtained. Methods for obtaining L-forms are described by J. C. Makemson and R. Z. Darwish (*Infect. Immun.* 6:880 (1972)) where the appropriate levels of calcium and magnesium ions are detailed for the efficient conversion of *E. coli* into L-forms is suitable for *E. coli*. Such induction is typically done through the use of an antibiotic such as penicillin. L-like mutants can be obtained from *E. coli* strains through specific mutations. For example, V. V. Androsov and V. S. Levashev (*Mikrobiologiya b* 44:435 (1975) — p. 386–391 in the English translation, *Microbiology*) describe a method involving treatment of *E. coli* K-12 strains Hfrc, J62, and P678 with N-nitroso-N-methylurea. The resulting mutants would be cultured in a minimal medium. For penicillin induction of L-forms the cells could be grown to fairly high densities (e.g., $10^{10}$ cells/ml), then treated by a method of Makemson and Darwish, and then immobilized. For mutants which are L-like, cultures could be grown from a low cell density since the mutation process would yield directly only a small fraction of the total population with the desired properties.

Similar procedures can be applied to other bacteria (see L. B. Guze, *Microbial Protoplasts, Spheroplasts, and L-Forms*, Williams & Wilkins Co., Baltimore, Md. (1968); G. F. Abbate, et al., *Chemotherapy* 19:341 (1973); M. R. DeCastro-Costa and O. E. Landmann, *J. Bacteriol.* 129:678 (1977).

As an alternative to removing the outer envelope, a periplasmic-leaky mutant bacterium can be used as the host bacterium. Periplasmic-leaky mutants can be obtained by known methods such as by mutagenesis (e.g., nitrosoguanidine) followed by in situ plate assays for detecting excretion of enzymes such as alkaline phosphatase, RNase I, or β-galactosidase. See, for example, J. C. Lazzaroni and R. C. Portalier (*FEMS Microbial. Lett.* 5:411–416 (1979)). Examples of different types of leaky mutants are described by J. J. Anderson, J. M. Wilson, and D. L. Oxender (*J. Bacteriol.* 140:351–358 (1979)); J. T. Fung, J. MacAlister, and L. I. Rothfield (*J. Bacteriol.* 133:1467–1471 (1978)); L. M. Havekes, B. J. J. Lugtenberg, and W. P. M. Hoekstra (*Mol. Gen. Genet.* 146:43–50 (1976)); Y. Hirota, H. Suzuki, Y. Nishimura, and S. Yasuda (*Proc. Nat'l Acad. Sci. U.S.A.* 74:1417–1420 (1977)); J. C. Lazzaroni and R. C. Portalier (*J. Bacteriol.* 145:1351–1358 (1981)); J. Lopes, S. Gottfried, and L. Rothfield (*J. Bacteriol.* 109:520–525 (1972)); and D. W. Yam and H. C. Wu (*J. Bacteriol.* 133:1419–1426 (1978)). In *E. coli* RB791 (*E. coli* W3110, F⁻, λ⁻, dam-3, lac I$^q$ L8) R. Brent and M. Ptashne, *Proc. Nat. Acad. Sci., U.S.A.* 78:4204 (1981) the induction of large amounts of protein from a plasmid encoded protein on a β-lactamase signal can interfere with normal outer membrane synthesis and lead to leaky-type behavior. This latter situation, wherein the bacterium is normally not leaky but exhibits leaky-type behavior when a high level of recombinant protein synthesis is induced, is believed to be due to a limited number of sites for protein transport through the inner membrane; when the plasmid is turned on, its products out compete the normal outer membrane proteins for secretion sites. Consequently, the outer membrane leaks because there is insufficient protein to complete its formation.

Production of leaky-type behavior is achieved by inducing a strong promoter on a high copy number plasmid. The induction is most effective for use in this invention if it occurs during late exponential growth (about one to two division times prior to the exhaustion of nutrient). Too early of induction can lead to cell death. If induction is done too late and no cell replication is allowed, leakiness will not develop. Leakiness has been observed in *E. coli* RB791 containing plasmid. Not all strains of bacteria, nor all *E. coli*, will work. Examples of other reports of leakiness in other *E. coli*-plasmid systems are given by K. Willemot and P. Cornelis, *J. Gen. Microbiol.* 129:311 (1983) and T. Kudo, C. Kato, and K. Horikoshi, *J. Bacteriol.* 156:949 (1983).

In accordance with the present invention, the bacteria can be immobilized by entrapment in a gel matrix to provide physical protection to the cells. Entrapment in the gel matrix is particularly suitable for gram-negative bacteria having all or part of the outer membrane removed, as such bacterial forms are fragile and entrapment provides protection from liquid shear and the like. The bacteria are entrapped in a matrix by mixing a concentrated cell solution with a dissolved gelling agent and then passing the mixture through small-diameter needles to form drops which fall into a solution which causes the gelling agent to polymerize forming a roughly spherical shape particle. Examples and variations of this are given by P. Brodelius and K. Mosback (*Adv. Appl. Microbiol.* 28:1–25 (1982)); by J. Klein, J. Stock, and K.-D. Vorlop (*Eur. J. Appl. Microbiol. Biotechnol.* 18:86–91 (1983)), the disclosures of which are herein incorporated by reference.

Substances which can be used as a matrix for entrapping the bacteria include agar, alginate, κ-carragean, polyacrylamide, agarose, or other polymers capable of gelling at physiological conditions.

Other forms of cell immobilization include adsorption onto solids and covalent linkage (J. M. Navarro and G. Durand, *Eur. J. Appl. Microbiol. Biotechnol.* 4:243 (1977)). Generally, the bacteria can be immobilized by entrapment or attachment within or onto a solid support which may be a gel, a polymer, a ceramic or glass, or a natural substance such as wood chips. Any mechanism for retaining most cells within the reactor would allow practice of the invention.

Immobilization can also be obtained by retaining the cells between membranes with pore sizes smaller than the bacteria but sufficiently large to allow the rapid transport of proteins across the membrane. Such devices are well known and are commercially available (e.g., Amicon, Millipore, and Dorr-Oliver) for use in ultrafiltration and dialysis. For examples, see J. Kan and M. L. Shuler, *Biotechnol. Bioeng.* 20:217 (1978).

Before, after, or simultaneously with inducing protein synthesis from the vector, the host cells are subjected to nutrient and/or temperature conditions that substantially inhibit host cell replication as defined above. Those cells which become leaky upon induction are generally best induced prior to immobilization since some increase in cell mass is necessary for leakiness to develop. Conditions that substantially inhibit host cell replication are readily determined by one of ordinary skill in the art and include nutrient limitation by a factor not directly required for protein synthesis (e.g., phosphate, iron, thymidine, etc.) and temperature.

In accordance with the present invention, the method of inducing the bacteria to produce proteins depends upon the particular inducer employed. Further, the conditons inducing the promoter can be the same as the conditions that inhibit cell replication or the conditions inducing the promoter can be different from the conditions that inhibit cell replication.

For example, if the inducible promoter is nutrient starvation activated, the non-replicating cell can be cultured in the absence of the nutrient. If the inducible promoter is temperature activated, i.e., temperature-sensitive, the non-replicating cell can be cultured at the temperature nonpermissive for cell growth but permissive for production of the desired protein. If the inducible promoter is chemically activated the non-replicating cells can be cultured in the presence of the inducing chemical but under nutrient and/or temperature conditions severely limiting cell replication.

Additionally, when the bacteria are immobilized in a gel matrix or membrane device, the feed stream must contain sufficient small molecular weight species in solution so that the osmotic pressure inside the cell will not cause cell lysis. A suitable temperature for *E. coli* will generally be between 20° to 45° C. (typically 37° C.) depending on whether a temperature-sensitive strain is used or not and depending on the economic balance between stability (low temperature improves physiological stability) and reaction rate for protein production (increases with temperature until the rate of denaturation becomes too high; for normal cells 25° to 37° C. results in a fairly stable system with rapid reaction rate).

13

For single cell organisms other than *E. coli*, different temperature ranges and optimums might occur. These temperature ranges and optimums are readily determined by one of ordinary skill in the art.

If phosphate starvation or a chemical inducer are to be used, the following type of medium would be appropriate: a modified A-P medium—12.1 g/l Tris buffer; 1.0 g/l $NH_4SO_4$, 0.1 g/l $MgSO_4.7H_2O$; fructose (2 g/l), a defined amino acid supplement (2 g/l) can be advantageous; 0.03 g/l $Na_3$ citrate.$2H_2O$; 5 g/l $CaCl_2$; with adjustment of pH to 7.5±0.5 with HCl. The above medium is effective with *E. coli* and will be acceptable with many other bacterial systems. The specific formulation of a practical medium for any single cell organism can be accomplished with slight modifications to any chemically defined medium used for such cells. For phosphate limitation in bacteria all phosphate is removed from the medium. If a phosphate buffer is normally used, it can be replaced with a Tris buffer or with a MOPS (3-[N-Morpholino] propanesulfonic acid) buffer. With systems using Ca-alginate immobilization the medium should have a high calcium content and low concentrations of chelators to prevent dissolution of the beads. If a chemical inducer is used (e.g., IPTG at $10^{-4}M$), it is added to the production medium.

As is clear from the description herein, the present invention is more compatible with lower-cost, higher-volume proteins than the method of Mosbach et al, supra.

The invention will now be described by reference to non-limiting examples.

EXAMPLE

Figure 1:
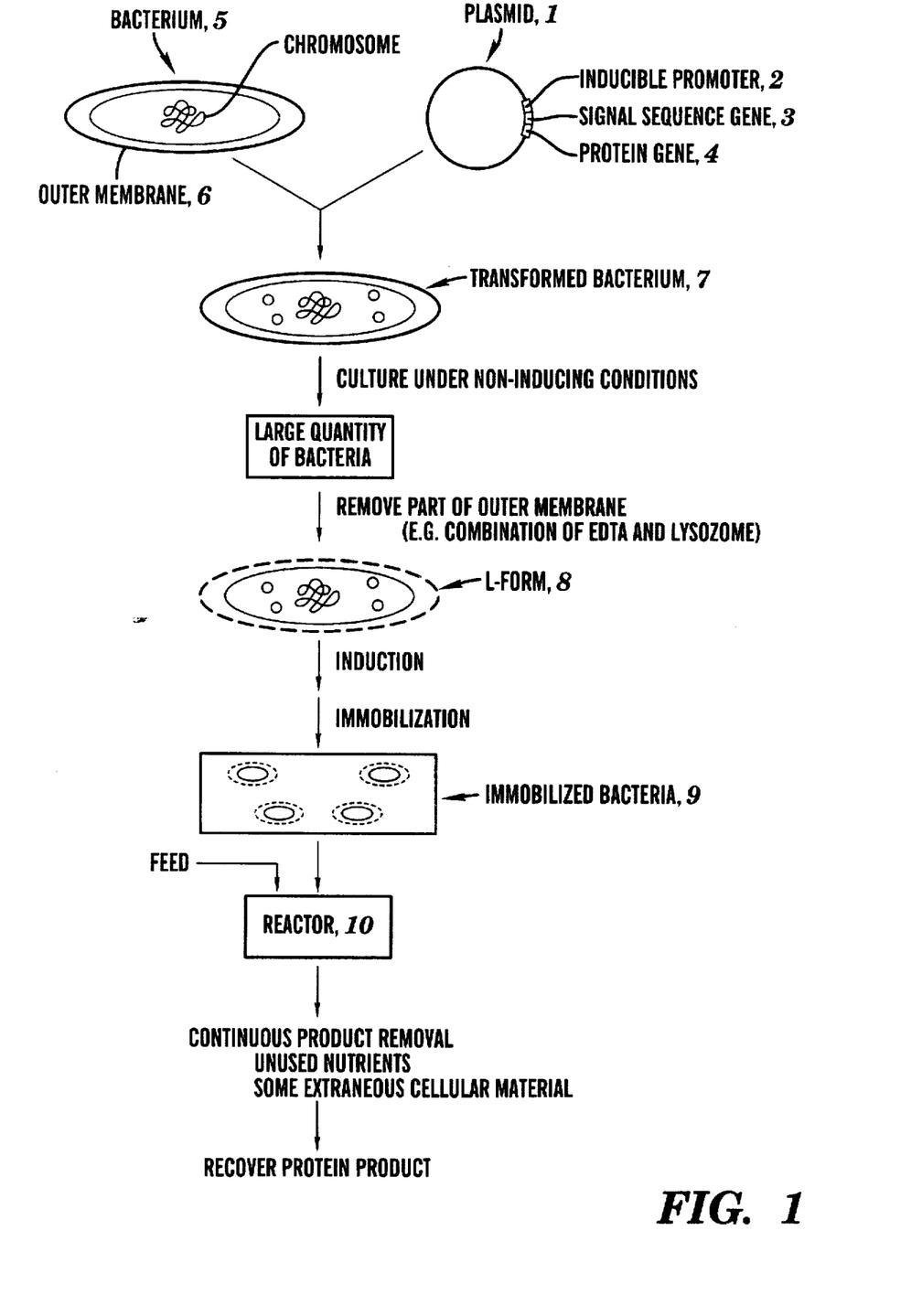
Figure 2:
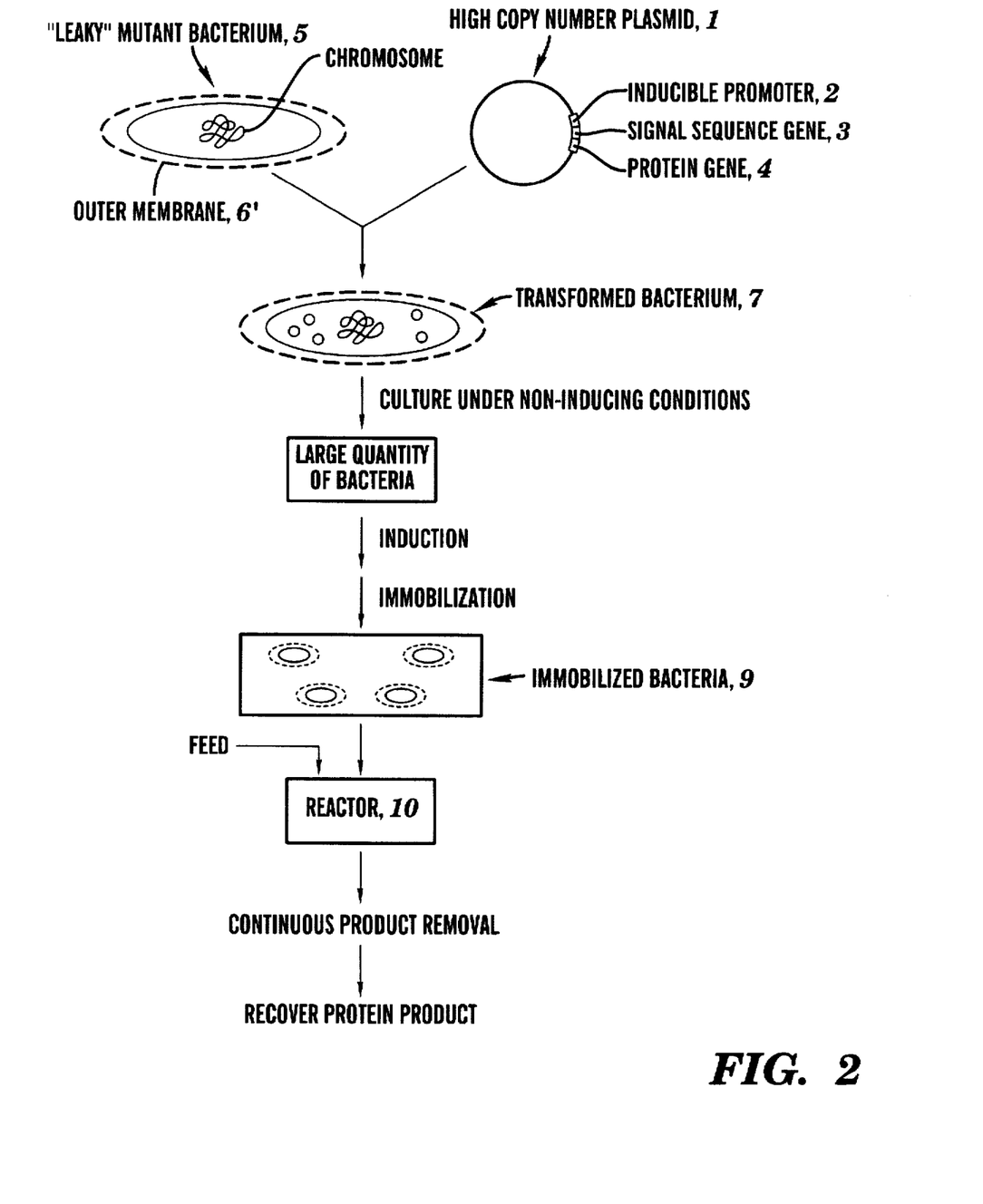
FIG. 2 is a second embodiment of the present invention wherein the bacterium 5 is a leaky mutant, having an incomplete outer membrane 6'. In this embodiment, the bacteria can be entrapped in a gel matrix or a hollow fiber unit to form immobilized bacteria, 9, without the step of removing the outer membrane as in the embodiment shown in FIG. 1.
Figure 3:
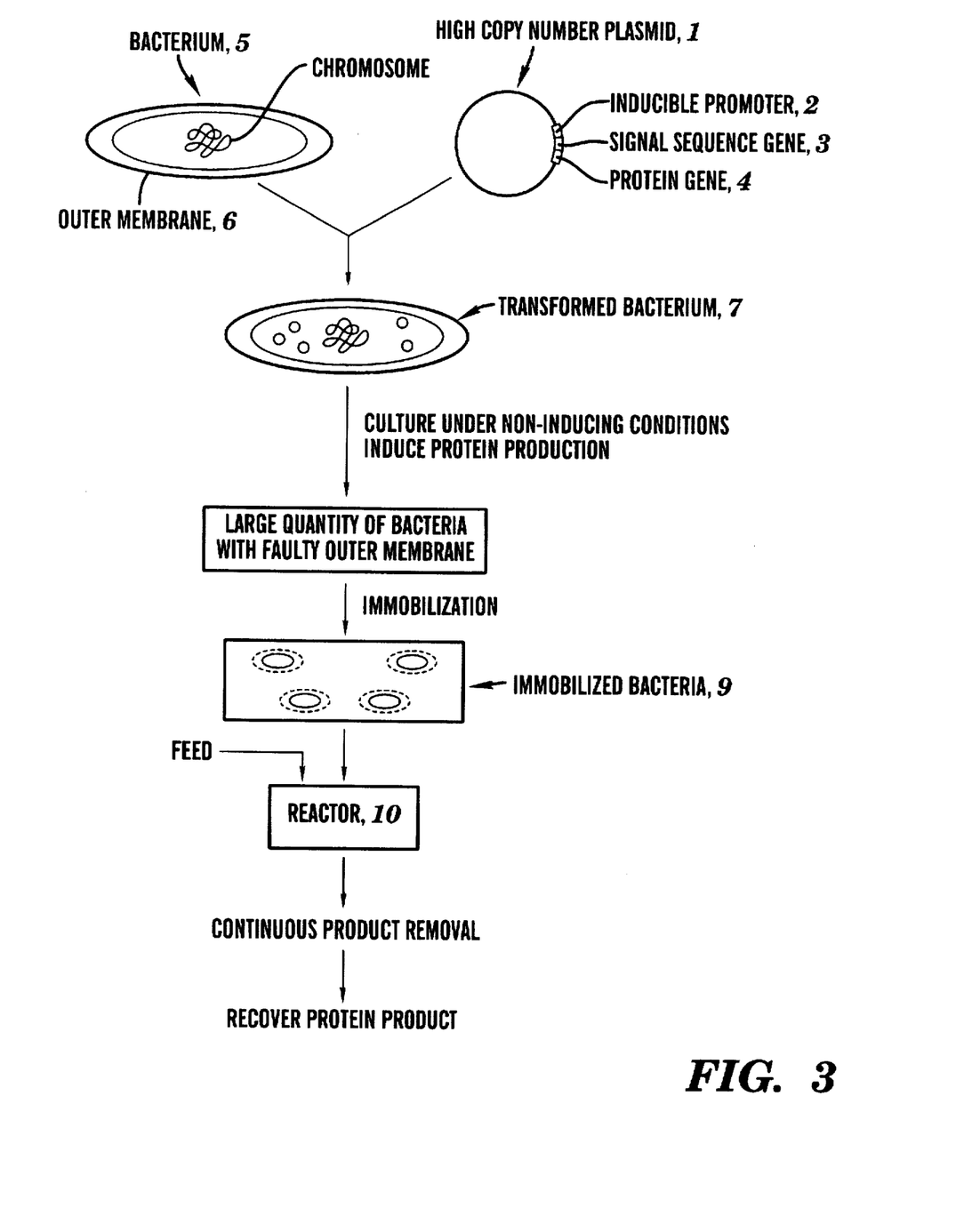

Conditions to induce leakiness in a normal cell (see FIG. 3).

The host cell is *E. coli* RB791 which is *E. coli* W3110 lac I$^q$L$_8$. This strain has been constructed by R. Brent and M. Ptashne, *Proc. Nat. Acad. Sci., U.S.A.*, 78:4204 (1981). The pedigree of *E. coli* W3110 is described by B. J. Bachmann, *Bacteriological Reviews*, 36:525 (1972). The pKK plasmid is essentially a pBR322 plasmid modified by the placement of a tac promoter upstream from the normal β-lactamase gene. This construction effectively couples the strong inducible tac promoter to the signal sequence for β-lactamase and the structural part of the β-lactamase gene. The pKK plasmid was inserted into the cell using the standard calcium transformation procedure (T. Maniatis, et al., *Molecular Cloning*, Cold Spring Harbor Laboratory (1982)).

To determine whether induction in the β-lactamase genes on the plasmid will lead to leaky-like behavior the following experiment was performed. Cells were grown under noninducing conditions (M9 medium—$Na_2HPO_4$ 6 g/l $KH_2PO_4$ 3 g/l; NaCl 0.5 g/l; $NH_4Cl$ 1 g/l; 2 ml/l of 1M $MgSO_4$; and 0.1 ml/l of 1M $CaCl_2$; 2 g/l fructose; 50 mg/l ampicillin; 2 g/l casein amino acids). T. Maniatis, E. F. Fritsch, and J. Sambrook, *Molecular Cloning*, Cold Spring Harbor Laboratory (1982). The optical density of the culture was measured at 600 nm, and the culture was induced at various O.D.$_{600}$ (optical density at a wavelength of 600 nm using a cuvette having a 1 cm path length) values with $10^{-4}M$ IPTG. Ten ml samples were removed and centrifuged at 7000 rpm for 8 minutes. The pellets were suspended in 3 ml phosphate buffer pH 7.0, broken in a French press and centrifuged at 10,000 rpm for 10 minutes. The extracts and supernatants were assayed for β-lactamase activity, β-galactosidase activity and total protein (by the method of M. Bradford, *Anal. Biochem.* 72:248 (1976).

14

The results are given in Table I.

TABLE I

| | Distribution of enzymatic activities | |
|---|---|---|
| Induction at OD$_{600}$ | β-Lactamase Extracellular Activity %* | β-galactosidase Extracellular Activity %* |
| 1) Uninduced | 5% | — |
| 2) 0.150 | 90% | 35% |
| 3) 0.360 | 79% | 11.5% |
| 4) 0.450 | 80% | 13.5% |
| 5) 0.620 | 44% | 3% |
| 6) 0.720 | 30% | — |

*% of total specific activity

Early induction promotes β-lactamase excretion at the expense of increased cell lysis and death as indicated by β-galactosidase extracellular activity.

Further, about 50% of the excreted protein was β-lactamase, thereby simplifying protein recovery. The levels of excretion achieved in Table I are comparable to those for leaky-mutants (N. Fognini-Lefebvre and R. Portalier, *C.R. Acad. Sci.* (Paris) t. 296, Serie III, 119–122 (1983).

The procedure described above allows the use of cells more robust than normal leaky-mutants.

All immobilization experiments were accomplished under aseptic conditions. For immobilization experiments, the following procedure was used:

1. *E. coli* RB791 containing pKK were grown in M-9 medium in a standard laboratory fermenter (1 l working volume) with full aeration and at 37° C. At a cellular O.D. (optical density) of about 0.50±0.15 (the O.D. was 0.63 in Trial 1 and the O.D. was 0.44 in Trial 2) the culture was induced by adding IPTG to give a concentration of 1×10$^{-4}$M. The culture was then allowed to grow for a period of time approximately equal to the doubling time (e.g., to an O.D. of about 1.3 in Trial 1).

2. The culture was harvested and concentrated by centrifugation at 5000 rpm for 15 minutes. A cell suspension 10-fold concentrated from the original suspension was obtained from the cell pellet. In both Trial 1 and 2 the concentrated cell suspension was then mixed in equal parts with an alginate suspension. The alginate solution was made by dissolving alginic acid (92% aq sol. has a viscosity of 3500 cps) in distilled $H_2O$ to give a 2% solution (by weight) when mixed with the cell solution. The cell-alginate solution was then pumped through a No. 25 gauge stainless steel needle. The solution formed drops which fell into a 5% $CaCl_2$ solution in Trial 1 and a 2% $CaCl_2$ solution in Trial 2. The $Ca^{++}$ ions initiated very rapid gelation of the alginate to form beads (2.2 mm±0.5 mm in diameter).

3. In Trial 1 approximately 5,500 beads were placed in a presterilized glass vertical fluidized bed rector with a total working volume of 110 ml which included 80 ml of free fluid. The reaction chamber was 18 cm high and 4 cm in diameter. Glass beads (7 mm in diameter) filled the lower 2.5 cm of the chamber and were present to disperse air sparged into the bottom of the chamber. Air was filter sterilized and entered the reactor at a flow sufficiently high to fluidize the beads (i.e., to cause circulation of the beads throughout the liquid phase).

The liquid medium fed to the reactor consisted of 12.1 g Tris base; 0.03 g $Na_3$ Citrate.$2H_2O$; 1.0 g $(NH_4)_2SO_4$; 0.1 g $MgSO_4.7H_2O$; 2.0 g fructose; 2.0 g casein amino acids; 5.0 g $CaCl_2$; and 0.05 g ampicillin in 1 l distilled $H_2O$. IPTG was added to a level of $5×10^{-5}M$. Some phosphate is contained in the natural amino acid digest.

Figure 4:
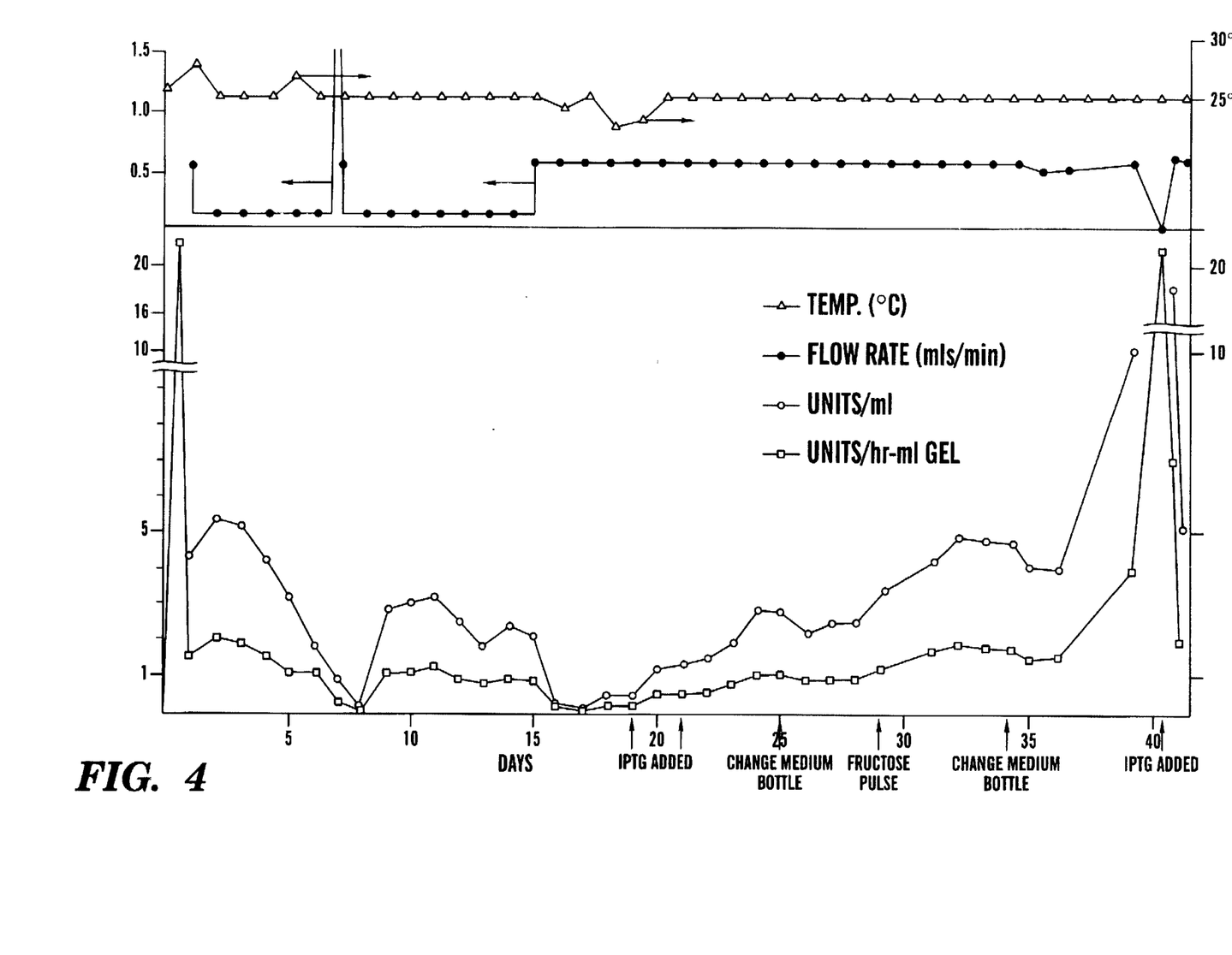
FIG. 4 and FIG. 5 are graphs demonstrating the superior protein production of the present system.

During start-up, a high flow rate of 5.6 ml/minute was pumped into the system to wash out surface attached cells. After 30 minutes a flow rate of 0.56 ml/minute was established. The flow rate was varied purposely as described in FIG. 4. At day 19 IPTG was pulsed into the system. The system responded with a five-fold increase in β-lactamase production. A pulse of IPTG at day 21 resulted in only a slight increase (10%) indicating that the cells were still fully induced from the first pulse even though most of the original IPTG had washed out. This response indicates that the cells are still metabolically active and under cellular control. New medium bottles were added at days 25 and 34. Fresh medium contains active undegraded IPTG. A fructose pulse of 1 ml of 20% fructose at day 29 appears to have also increased production. The cells in the center of the bead may be starved for nutrients due to mass transfer limitations. A pulse of IPTG or fructose allows these chemicals to penetrate further into the beads, possibly activating cells which would be otherwise metabolically dormant. A higher flow rate to the system provides a greater input of nutrients and the higher flow rate after day 15 may also be involved in the improving performance of the reactor. At day 39 the influent flow was stopped for about 15 hours. Product accumulated fairly rapidly. Normally, the effluent is clear (optical density at 600 nm less than 0.05) but, the culture became turbid under non-flow conditions indicating the slow release of cells from the beads. The system appears to have returned to its previous operational status by day 41. The main conclusion from this trial is that protein production and excretion can be sustained for long periods. The system was still operating up to 54 days later. The projected lifetime of the reactor is difficult to predict, but is projected to last substantially in excess of 2 months.

4. In Trial 2, a similar procedure and reaction vessel were used. The main differences were (1) a 2% Ca solution was used to form the beads and (2) a defined amino acid mixture was used (i.e., see list below in Table II) in place of casein amino acids to insure that no phosphate was added to the medium. A constant fow rate of 32 ml/h was used and the total working volume of the reactor was 130 ml.

Figure 5:
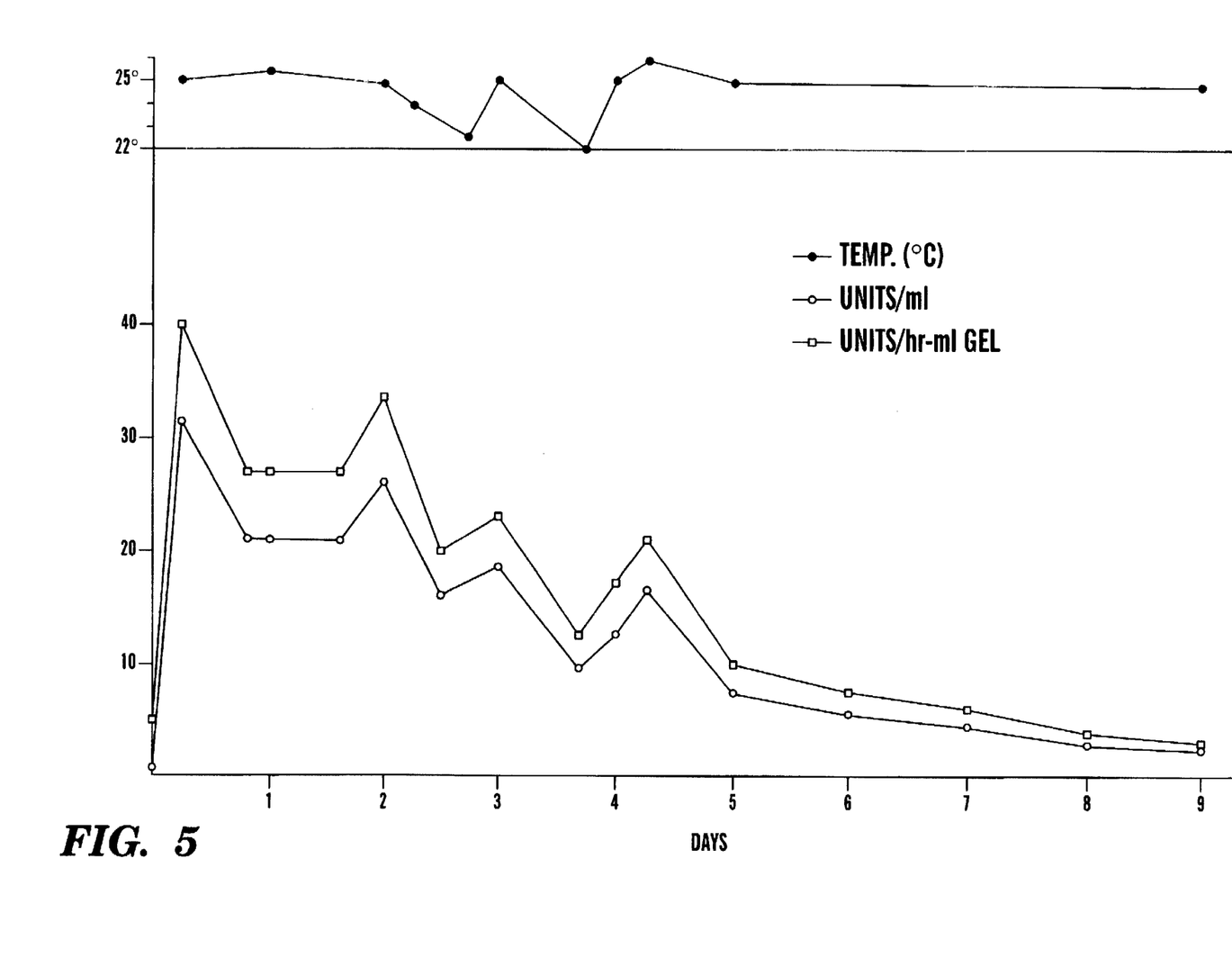

The results of the experiment are given in FIG. 5. The productivity of this system is much greater than the one with 5.0% $CaCl_2$, possibly because the beads were made with less $Ca^{++}$ which allowed better transfer of nutrients into and out of the cells. At day 9 the influent medium was altered by the addition of a low level of phosphate (0.002 g/l P). Contamination in the reactor was observed within 14 hours and the run was then terminated.

TABLE II

| Amino Acid | g/100 ml |
| --- | --- |
| Alanine | 0.84 |
| Arginine | 2.53 |
| Asparagine | 0.84 |
| Aspartate | 1.0 |
| Cysteine | 0.73 |
| Glutamine | 14.6 |
| Gylcine | 0.2 |
| Histidine | 0.31 |
| Isoleucine | 0.79 |
| Leucine | 0.79 |
| Lysine | 1.1 |
| Methionine | 0.9 |
| Phenylalanine | 0.99 |
| Proline | 4.6 |
| Serine | 8.4 |
| Thiamine | 0.337 |
| Threonine | 0.71 |

TABLE II-continued

| Amino Acid | g/100 ml |
| --- | --- |
| Tryptophan | 0.41 |
| Tyrosine | 0.36 |
| Valine | 0.7 |

These results can be compared to those reported by K. Mosbach, et al., *Nature* 302:543 (1983) for cells of *Bacillus subtilis* immobilized in agarose gel beads and producing rat proinsulin in a medium containing the antibiotic novobiocin to prevent cell replication. The results from Trial 1 and Trial 2 are unexpectedly superior; Mosbach, et al., report proinsulin production for only 3.3 days (e.g., 8.0 hours) in a continuous reactor whereas in Trial 1 production has been sustained for more than 54 days and in Trial 2 for 9 days. Mosbach, et al., used *B. subtilis* to enhance excretion but proteases released simultaneously destroyed the protein product—a problem avoided in the present approach by using *E. coli*. In the Mosbach, et al., reactor at day 3, protein was produced at a rate of about 1.6 ng/ml per hour. In Trial 2 at day 3, the present reactor produced about 1.6 μg/ml per hour assuming 1 mg β-lactamase gives 3500 units of activity. In Trial 1 at day 41 the system was producing about 0.5 μg/ml per hour of β-lactamase. Thus, the present system produced about 1000-fold more protein per unit reactor volume per unit time and sustained production at these rates for a much longer period of time than the Mosbach et al system.

While the invention has been described in detail and with reference to specific embodiments thereof, it will be apparent to one skilled in the art that various changes and modifications can be made therein without departing from the spirit and scope thereof.

We claim:

1. A method for producing a protein, said method comprising:
   providing non-leaky cells comprising a gene encoding a protein and an inducible promoter controlling expression of the gene;
   culturing the non-leaky cells under conditions effective for the non-leaky cells to undergo exponential growth; and
   inducing protein expression in the exponentially growing non-leaky cells at expression levels effective to prevent complete formation of outer membranes of the exponentially growing cells, whereby leaky cells are formed and protein is released from the leaky cells.

2. A method according to claim 1, wherein the cells are bacterial cells.

3. A method according to claim 2, wherein the bacterial cells are Gram negative.

4. A method according to claim 2, wherein the bacterial cells are selected from the group consisting of *Pseudomonas putida*, *Pseudomonas olevorans*, and *Escherichia coli*.

5. A method according to claim 4, wherein the bacterial cells are an *Escherichia coli* K-12 strain.

6. A method according to claim 1, wherein the protein is one which passes through inner membranes but not outer membranes of the non-leaky cells.

7. A method according to claim 1, wherein the cell further comprises DNA encoding a signal sequence, expression of which is effective to permit the protein to pass through inner membranes of the non-leaky cells.

8. A method according to claim 7, wherein the signal sequence is a beta-lactamase signal sequence.

9. A method according to claim 1, wherein the inducible promoter is a temperature inducible promoter.

10. A method according to claim 1, wherein the inducible promoter is a chemically inducible promoter.

11. A method according to claim 1, wherein the inducible promoter is a phosphate starvation inducible promoter.

12. A method according to claim 11, wherein the phosphate starvation inducible promoter is a Pho A promoter.

13. A method according to claim 1, further comprising:

continuing to induce protein expression in the leaky cells under conditions effective substantially to inhibit further exponential growth of said cells.

14. A method according to claim 1, further comprising:

continuing to induce protein expression in the leaky cells at an expression level effective substantially to inhibit further exponential growth of said cells.

15. A method according to claim 1, wherein protein released from the leaky cells enters a culture medium containing the leaky cells and wherein said method further comprises:

recovering the protein from the culture medium.

16. A method according to claim 1, further comprising:

immobilizing the leaky cells.

17. A method according to claim 16, wherein the leaky cells are entrapped in a gel matrix.

18. A method according to claim 16, wherein the leaky cells are covalently bonded to a solid support.

19. A method according to claim 16, wherein the leaky cells are adsorbed onto a solid support.

20. A method according to claim 1, wherein the leaky cells are retained between devices having pores sized to retain the leaky cells and to pass the protein.

21. A method according to claim 1, further comprising:

continuing to induce expression of the protein in the immobilized leaky cells under conditions effective substantially to inhibit further cell replication.

22. A method for producing leaky cells, said method comprising:

providing non-leaky cells comprising a gene encoding a protein and an inducible promoter controlling expression of the gene;

culturing the non-leaky cells under conditions effective for the non-leaky cells to undergo exponential growth; and inducing protein expression in the exponentially growing non-leaky cells at expression levels effective to prevent complete formation of outer membranes of the exponentially growing cells, whereby leaky cells are formed.

23. A method for producing a protein, said method comprising:

providing leaky cells produced according to claim 22; and inducing expression of a protein in the leaky cells, whereby the protein is released from the leaky cells.

24. A method according to claim 23, wherein said inducing expression of a protein is effected under conditions effective substantially to inhibit further exponential growth of said cells.

* * * * *